United States Patent [19]
Ohshima et al.

[11] Patent Number: 5,534,698
[45] Date of Patent: Jul. 9, 1996

[54] SOLID STATE SURFACE EVALUATION METHODS AND DEVICES

[75] Inventors: Hisayoshi Ohshima; Yoshiyasu Yamada, both of Kariya, Japan

[73] Assignees: Research Development Corporation, Saitama; Nippon Denso Co., Ltd., Aichi, both of Japan

[21] Appl. No.: 271,741

[22] Filed: Jul. 7, 1994

[30] Foreign Application Priority Data

Jul. 7, 1993 [JP] Japan .................................. 5-168217
Dec. 27, 1993 [JP] Japan .................................. 5-329388

[51] Int. Cl.$^6$ .................................................. G01J 3/42
[52] U.S. Cl. ........................ 250/339.11; 250/339.07; 250/341.3; 250/341.1; 250/341.8
[58] Field of Search .................... 250/339.07, 339.08, 250/339.11, 341.4, 341.8, 358.1, 353, 341.3; 356/239, 432

[56] References Cited

U.S. PATENT DOCUMENTS

| | | | |
|---|---|---|---|
| 3,475,615 | 10/1969 | Samuel | 356/239 |
| 4,511,800 | 4/1985 | Harbeke et al. | 250/358.1 X |
| 4,594,509 | 6/1986 | Simon et al. | 250/353 X |
| 5,077,475 | 12/1991 | Moriya et al. | 250/341.4 X |
| 5,321,264 | 6/1994 | Kuwabara et al. | 250/339.12 X |

OTHER PUBLICATIONS

Olsen et al., "Infrared reflection spectroscopy of the $SiO_2$-silicon interface", pp. 1353–1358, Journal of Applied Physics, vol. 66, No. 3, Aug. 1, 1989.

Ling et al., "Multiple internal Reflection infrared spectroscopy of silicon surface structure and oxidation process at room temperature", pp. 3018–3022 Journal of Applied Physics, vol. 73, No. 6, Mar. 15, 1993.

Jakob et al., "Chemical etching of vicinal Si(111): Dependence of the surface structure and the hydrogen termination of the pH of the etching solutions", pp. 2897–2909 Journal of Chemical Physics, vol. 95, No. 4. Aug. 15, 1991.

Bermudez, "Infrared spectroscopic study of the chemisorption of $CF_3$ species on silicon", pp. 3297–3299 Appl. Phys. 62, No. 25, Jun. 21, 1993.

Ohshima et al., "Novel Technique of Infrared Reflection Absorption Spectroscopy for Si Surface Study", pp. L1176–L1178, Journal of Applied Physics, vol. 32, Part 2, No. 8B, Aug. 15, 1993.

*Primary Examiner*—Carolyn E. Fields
*Assistant Examiner*—Edward J. Glick
*Attorney, Agent, or Firm*—Wenderoth, Lind & Ponack

[57] ABSTRACT

Methods and devices for evaluating solid-state surface properties use infrared absorption of lattice vibration. These methods and devices are characterized by reflection spectrometry by injecting infrared rays from the reverse of the solids, placing a light transmissible solid-state sample in ways that its surface faces the plane reflex mirror on the interaction region formed by reflected infrared rays, or by injecting infrared rays from the rear of a sample or from the front thereof after upright installation of the light transmissible solid-state sample through a slit created across the plane reflex mirror or on the surface of plane reflex mirror. These methods and devices enable simplified and accurate reflection spectrometry of solid-surface properties, featuring an economical system configuration that dispenses with expensive prism, unlike the conventional ATR method.

31 Claims, 3 Drawing Sheets

SOLID STATE SURFACE EVALUATION METHODS AND DEVICES

FIELD OF INVENTION

This invention relates to solid state surface evaluation methods and devices, more particularly to the innovative spectrometric evaluation methods and devices capable of analyzing solid state surface properties, as of semiconductors in a noncontact, easy and precise manner, and featuring more economical system configuration.

CONVENTIONAL TECHNOLOGIES

Recently, in the fields of electronic and chemical technologies, closer interest has been focused on the determination of solid state surface conditions more closely, specifically in terms of the atomic and molecular level. Extensive studies have been conducted on spectrometric evaluation techniques for solid state surfaces along with analysis thereof.

In particular, in the field of semiconductors, rigid surface controls on solid state, in terms of the atomic and molecular level, is becoming necessary following progress in finer circuit integration. It derives from the fact that clean semiconductor surface, as of a silicon wafer, features extremely high physicochemical activity and it tends to adsorb natural oxide film, organic matter, etc. Therefore, in order to eliminate the negative impact of such a highly activated surface and to inactivate it, a technique of hydrogen termination of surface dangling bonds after HF-treatment of a silicon surface has been developed.

However, in order to facilitate more rigid and precise control on surface, because a semiconductor surface features complex and diverse properties, it is becoming indispensable to develop a new method or technique to facilitate accurate evaluation of the surface condition itself. Accordingly, extensive studies have been conducted on relevant evaluation techniques or methods, but as of now, there remain outstanding problems that have yet to be resolved.

Specifically, for semiconductor evaluation, techniques aimed at utilizing absorption by means of optical transition commensurate to specific surface properties involved, in particular a variety of reflection spectrometric techniques, have been adopted as the major approach, because measurement by light transmission is not effective since surface-based absorption is commonly much lower than internal absorption.

Conventionally, infrared spectrometry has been employed for the evaluation of impurities in the bulk and film components of a thick film.

Recently, following the development of the Fourier-Transformation Infrared Reflection (FT-IR) spectrometric technique, infrared spectrometry is becoming common in use for the evaluation of semiconductor surface properties as one of the surface analysis techniques. Infrared spectrometry operates by combining special optical systems to enhance the sensitivity of the surface of a sample.

The Attenuated Total Reflection (ATR) technique can especially evaluate silicon surface properties with a high sensitivity by treating absorption in the crystal prism as background, because silicon itself, out of the semiconductor, acts as a crystal prism. Therefore, the ATR technique can reportedly measure the uppermost surface layer under the first atomic layer.

As exemplified in FIG. 5, it has been made possible to evaluate the surface properties of silicon wafers used fop LSI production by reflection spectrometry. Germanium is brought into contact with a silicon substrate 12 as a crystal prism 13, and infrared rays are injected from one of the inclined faces of the crystal prism 13.

However, such a technique has a number of problems in that an expensive prism needs to be used, the measured sample surface is brought into direct contact with the prism and a spectrum of 1000 cm-1 or less cannot be obtained from prism absorption itself.

Also, as an alternative, the Reflection Absorption Spectrometry (RAS) technique has been used for metal surface analysis, but in view of the fact that this technique cannot acquire the desired sensitivity regarding a semiconductor, metal is used as the base of the film semiconductor to evaluate its surface. In this case, too, a sample needs to be made according to custom specifications, which in turn can pose a problem with general purpose applications.

SUMMARY OF THE INVENTION

This invention has been devised taking such a situation into account. Specifically, the object of this invention is to provide new infrared spectrometric methods and devices capable of analyzing solid state surface, properties, e.g. of semiconductors, whose surface properties can be critically affected by the behavior of a catalyst, etc., in a noncontact, easy and precise manner and with a more economical system construction which dispenses with an expensive spectrometric prism and capable of acquiring extensive information on the solid state sample, as e.g. semiconductors.

The present invention evaluates solid surface properties by infrared absorption of lattice vibration as a way of resolving the above problems. The present invention provides the following two methods:

[1] a solid state surface evaluation method characterized by reflection spectrometry comprising injecting infrared rays from the reverse of the solids, and placing a light transmissible solid state sample in ways that its surface faces the plane reflex mirror in the interaction region formed by reflected infrared rays and,

[2] a solid state surface evaluation method characterized by reflection spectrometry comprising injecting infrared rays from the rear of a sample or from the front there:of after upright installation of the light transmissible solid state sample through a slit created across a plane reflex mirror or on the surface of the plane reflex mirror.

The present invention furthermore provides a solid state surface evaluation device that is equipped, for the application of method [1], with a light source, an injector, a plane reflex mirror and a reflex spectroscope. A light transmissible solid state sample is placed in ways that its surface faces the plane reflex mirror in the interaction region formed by reflected infrared rays, and the device performs reflection spectrometry by injecting infrared rays from the reverse of the solid state sample. The present invention also provides a solid state surface evaluation device that is equipped, for the application of the method [2], with a light source, an injector, a plane reflex mirror and a reflex spectroscope. The plane reflex mirror is provided with a slit for upright installation (or otherwise) of a sample to be measured, and with a support which holds upright a light transmissible sample through the slit in ways that its surface does not touch the slit or on the surface of the plane reflex mirror. The device performs reflection spectrometry by injecting infrared rays from the rear of the sample.

DETAILED DESCRIPTION OF THE INVENTION

The object of the present invention is to perform the following two types of full reflection spectrometry using plane reflex mirrors in a method designed to evaluate solid state surface properties by means of infrared absorption of lattice vibrations as mentioned in the preceding paragraphs. A first method of reflection spectrometry injects infrared rays from the reverse of solids, placing a light transmissible solid state sample in such a way that its surface faces the plane reflex mirror in an interaction region formed by reflected infrared rays. A second method of reflection spectrometry injects in rays from the rear of a light transmissible solid state sample after creating a slit thicker but not wider than a measured sample across a plane reflex mirror and after upright installation of the sample through the slit in such a way that its surface dose not touch the inner face of the slit.

The combined application of these methods can detect the components of absorbent molecular vibration on the sample surface in every direction.

This invention can dispense with the use of an expensive prism that is conventionally used for the Reflection Absorption Spectrometry (RAS) and the Attenuated Total Reflection (ATR) techniques and facilitates sample evaluation in a noncontact manner. The inventive method does not itself pose any problem with respect to prism absorption.

The inventive method can, in the second method, also evaluate the angular dependency of the elements of absorbent molecular vibration on the sample surface by changing a reflex mirror to sample angle. The inventive method can also measure two-dimensional distribution on the sample surface by relocating the sample or the plane reflex mirror since the detection area is limited.

Figure 4:
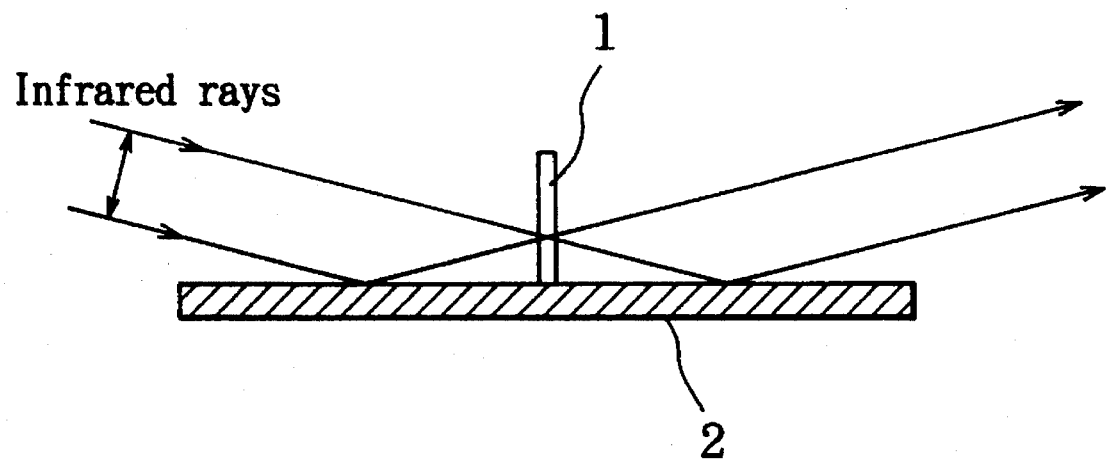
FIG. 4 is a schematic view which depicts an upright installation of a sample in a plane reflex mirror without a slit in a method and device embodying the present invention.
Figure 5:
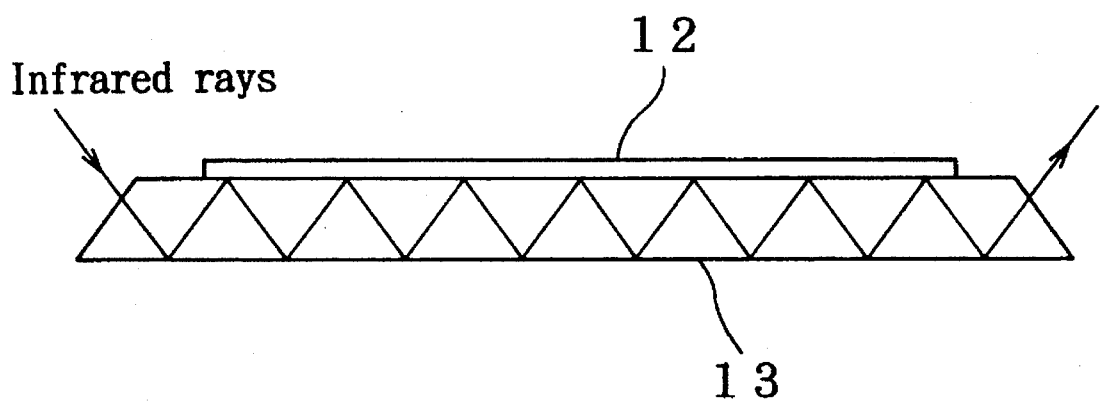
FIG. 5 is a schematic view which depicts an example of conventional methods.

In other words, the present invention enables system construction at lower costs and provides noncontact, simplified and accurate reflection spectrometry, and it can also measure the elements of absorbent molecular vibration on the sample surface in every direction, and determine angular dependency of molecular vibration components and their two-dimensional distribution.

Where a small sample is involved, similar measurement and evaluation is possible with the second method despite upright installation of a sample on the surface of the plane reflex mirror without a slit (FIG. 4).

The inventive method and devices enables evaluation of surface proper for semiconductors, and especially the evaluation of hydrogen, fluorine, nitrogen, and organic matters on the surfaces.

(EXAMPLE 1)

Figure 1:
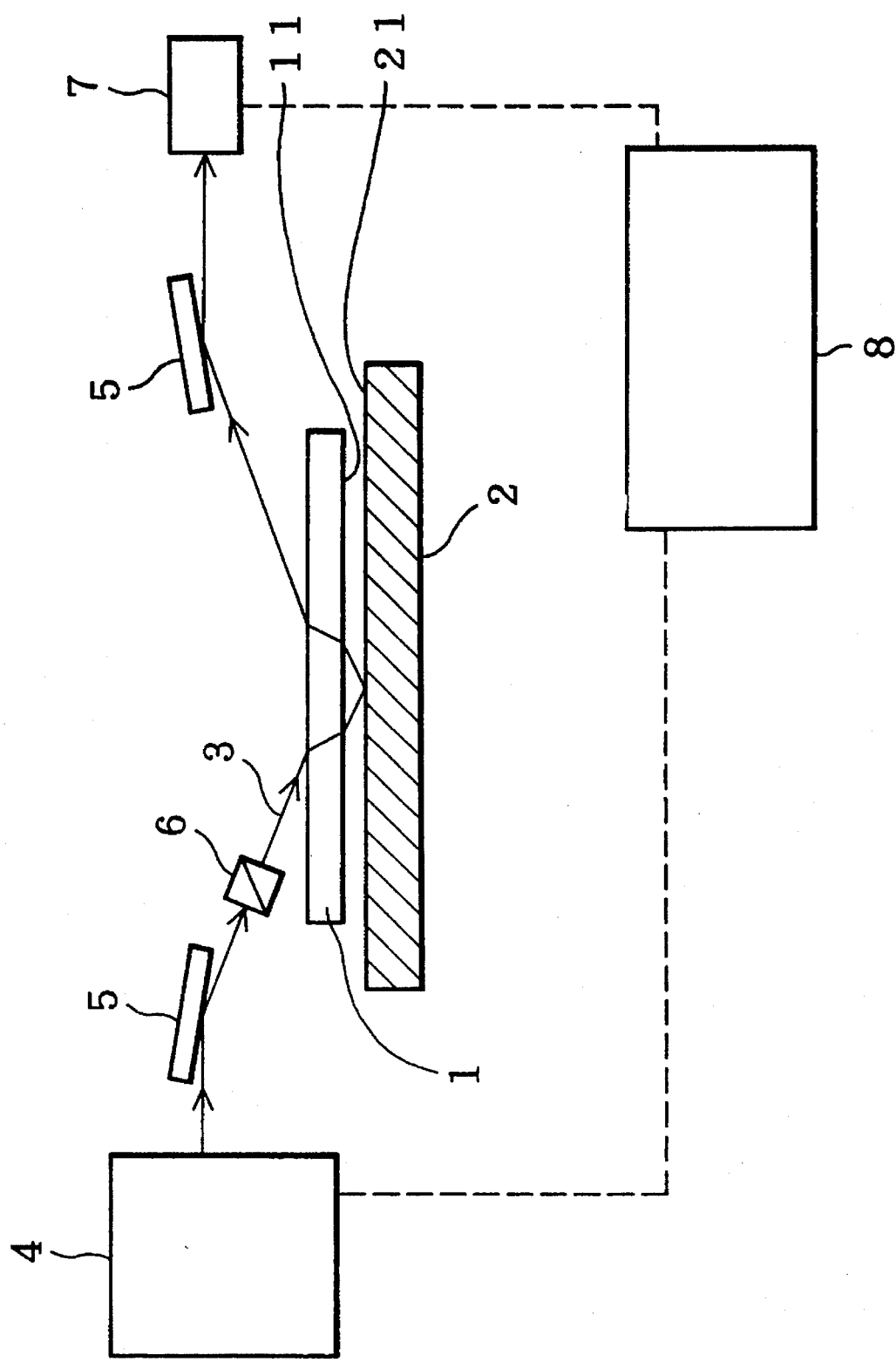
FIG. 1 is a schematic view which depicts an arrangement of a sample facing a plane reflex mirror in a method and device embodying the present invention.

FIG. 1 in the appended drawings is a schematic view of the first method [1] and major system components embodying this invention.

For instance, as exemplified in FIG. 1, this invention arranges an evaluated sample surface (11) of a light transmissible semiconductor (1) in such a way that it faces a plane reflex mirror (2). In this instance, the light transmissible semiconductor sample (1) may be common silicon or germanium semiconductors. Also, the common type of optical reflex mirrors can be used for plane reflex mirror (2) embodying this invention. For a reflector plate surface (21), gold, which sensitively reflects infrared rays, can be optimally used.

The evaluated surface (11) of the light transmissible semiconductor (1) is disposed apart from reflector plate (21) of the plane reflex mirror (2), with a spacing less than the infrared wavelength used. Ordinarily, the infrared wavelength used ranges from 2 to 20 μm. Therefore, the spacing should preferably be based on a value of less than 20 μm, but for higher sensitivity, the spacing should preferably be considered to be even further narrowed.

In such a system layout, infrared rays are injected at a low angle as in the RAS method from the rear of the light transmissible semiconductor sample (1) shown in FIG. 1., which shows an infrared path.

Noting attention to plane reflex mirror (2), an electric field is formed by regarding a p wave, and the surface sensitivity is gaining in this area, as in the case of the RAS technique. Since the region of the surface sensitivity extends from the surface, super sensitive measurement is possible provided that the sample surface is directed to this region.

It is recommended that an evaluation system should be composed of an infrared optical source and interferometer (4), reflect mirrors (5), a polarizer (6), a detector (7), an instrumentation computer (8), as in the case of common Fourier-Transformation Infrared Reflection Spectrometry (FT-IR), and, optionally, a amplifier and an processor as an arithmetic unit.

A support which secures the semiconductor (1) and the plane reflex mirror (2) in a specified position such as a, three-dimensional stage, etc., should be installed as required.

In fact, the method embodying this invention facilitates precise confirmation of the signal of symmetric stretching vibration (2083.7 cm$^{-1}$) as Si-H absorption due to hydrogen termination of dangling bond on the Si wafer surface, and also Si-H$_2$ (2107 cm$^{-1}$) absorption and oxygen combination/absorption.

(EXAMPLE 2)

Figure 2:
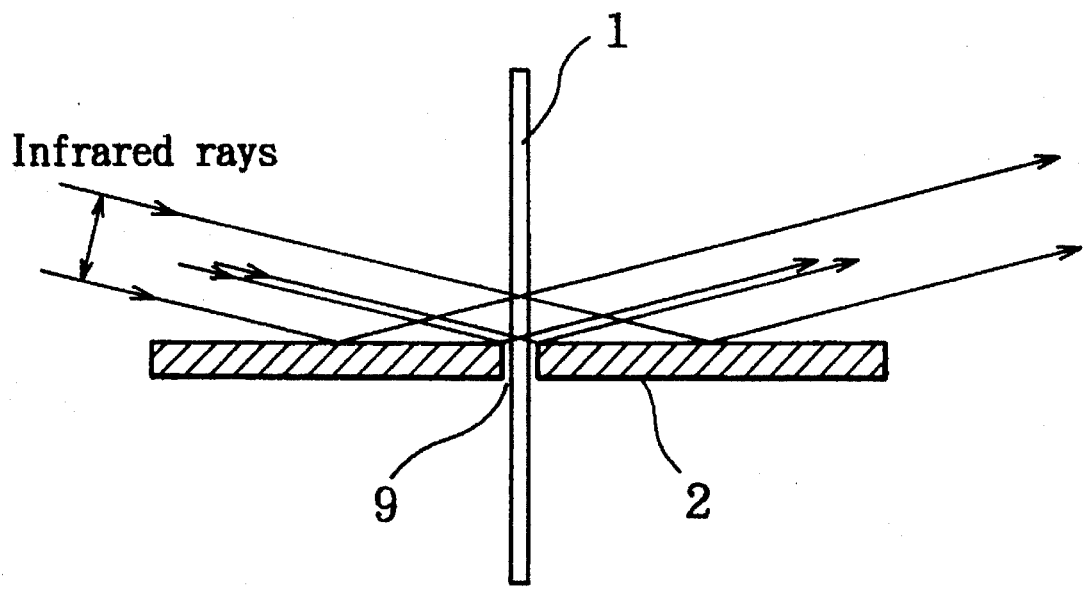
FIG. 2 is a schematic view which depicts an upright installation of a sample through a slit in a method and device embodying the present invention.

FIG. 2 in the appended drawings is a schematic view showing the second inventive method [2] and the major system configuration.

For instance, in this invention, the light transmissible semiconductor sample (1) is installed upright within a slit (9) inserted across the plane reflex mirror (2), as shown in FIG. 2.

For the purpose of this invention, any mirrors used for a common optical system may be used as the plane reflex mirror (2), but it is preferable to use an aluminum or gold reflector surface because it intensely reflects infrared rays.

It is preferable that the slit (9) of the plane reflex mirror (2) is wider than the thickness of a measured sample, but if it is excessively wide, it can lower detection sensitivity. In such a system arrangement, infrared rays are injected at a low angle from the rear of the sample or from the front thereof as shown in FIG. 2, as in the case of the RAS techniques.

In this instance, it is preferable to adjust the position of the slit (3) of the plane reflex mirror (2) to exist at the center of incident rays. Infrared rays run along the path illustrated in FIG. 2, and incident rays and reflexive rays are synthesized in the vicinity of the slit (9), followed by an increase in sensitivity in this region. Vectors synthesized on this occasion run in parallel with a sample surface. As a result, parallel components of molecular vibrations in this region are super-sensitively detectable.

Figure 3:
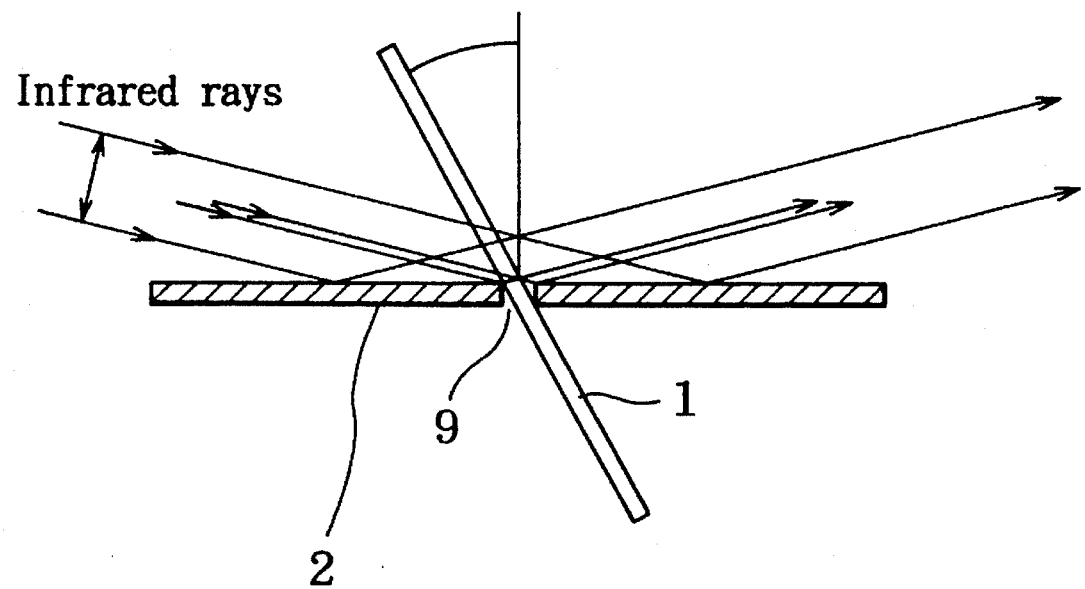
FIG. 3 is a schematic view which depicts a plane reflex mirror arranged at a modified angle with a sample in a method and device embodying the present invention.

As shown in FIG. 3, the angular dependency of the components of absorbent molecule vibrations on the sample surface (1) can be evaluated. As the detection area is limited, the two-dimensional distribution on the sample surface can also be determined by relocation of the sample (1) or the plane reflex mirror (2).

As in the case of Example 1, the evaluation system should be configured of an infrared light source, an interferometer, reflex mirrors, a polarizer, a detector and an instrumentation computer, and optionally including an amplifier, an arithmetic unit, etc.

Other options include the arrangement of a support, a three-dimensional stage, etc. as a means of installing the sample (1) and the plane reflex mirror (2) at specified positions.

The plane reflex mirror (2) with the slit (9) can be replaced by more than two plane reflex mirrors.

Where the sample used is small as compared to a silicon wafer, the sample may be laid on the plane reflex mirror without a slit, as indicated in FIG. 4

As detailed above, the present invention, which features a more economical system configuration, provides various useful information on solid state surface properties by means of reflection spectrometry that is available in an easy but accurate manner.

What is claimed is:

1. A method of evaluating solid state surface properties by infrared absorption of lattice vibration, the method comprising the steps of:

placing a light transmissible solid state sample having a sample surface and a reverse surface next to a plane reflex mirror such that the sample surface faces the plane reflex mirror;

projecting infrared rays at the reverse surface of the solid state sample such that an interaction region is formed by reflected infrared rays reflecting from the plane reflex mirror, the solid state sample being located in the interaction region; and evaluating the properties of the sample surface of the solid state sample by infrared reflection spectrometry of the reflected infrared rays.

2. The method of claim 1, wherein said step of projecting comprises projecting the infrared rays at the reverse surface of the solid state sample at an angle that is closer to parallel to the plane reflex mirror than to perpendicular to the plane reflex mirror.

3. The method of claim 1, wherein said step of placing comprises placing the light transmissible solid state sample next to the plane reflex mirror with a separation therebetween, the separation being less than the wavelength of the infrared rays.

4. The method of claim 1, Wherein said step of evaluating comprises receiving the reflected infrared rays with a detector connected to an instrumentation computer, the instrumentation computer performing infrared reflection spectrometry on the reflected infrared rays.

5. The method of claim 1, wherein said step of projecting comprises projecting the infrared rays from an infrared optical source and interferometer through a polarizer to the reverse surface of the solid state sample such that the infrared rays are transmitted through the solid state sample, reflected off of the plane reflex mirror and again transmitted through the solid state sample.

6. The method of claim 3, wherein said step of placing comprises placing a light transmissible solid state sample next to the plane reflex mirror with the separation being less than 20 μm.

7. The method of claim 1, wherein said step of placing comprises placing a light transmissible solid state sample having a semiconductor surface as the sample surface.

8. The method of claim 7, wherein said step of projecting comprises projecting the infrared rays at the reverse surface of the solid state sample at an angle that is closer to parallel to the plane reflex mirror than to perpendicular to the plane reflex mirror.

9. A method of evaluating solid state surface properties by infrared absorption of lattice vibration, the method comprising the steps of:

positioning a light transmissible solid state sample having a front surface and a reverse surface in an upright position relative to a plane reflex mirror;

projecting infrared rays at one of the front surface and the reverse surface of the solid state sample such that the infrared rays are reflected on the plane reflex mirror; and evaluating the properties of the solid state sample by infrared reflection spectrometry of the reflected infrared rays.

10. The method of claim 9, wherein said step of positioning comprises positioning the solid state sample so as to extend through a slit in the plane reflex mirror.

11. The method of claim 10, wherein said step of positioning comprises positioning the solid state sample so as to extend perpendicularly to the plane reflex mirror through the slit.

12. The method of claim 10, wherein said step of positioning comprises positioning the solid state sample so as to extend at an angle greater than 45° relative to the plane reflex mirror through the slit.

13. The method of claim 9, wherein said step of positioning comprises positioning the solid state sample on the plane reflex mirror.

14. The method of claim 13, wherein said step of positioning comprises positioning the solid state sample so as to extend perpendicularly from the plane reflex mirror.

15. The method of claim 9, wherein said step of projecting comprises projecting the infrared rays at the solid state sample at an angle that is closer to parallel to the plane reflex mirror than to perpendicular to the plane reflex mirror.

16. The method of claim 9, wherein said step of placing comprises placing a light transmissible solid state sample having a semiconductor surface as one of the front and reverse surfaces.

17. The method of claim 9, wherein the solid state sample and the plane reflex mirror have an area of intersection and said step of projecting comprises projecting the infrared rays at one of the front surface and the reverse surface of the solid state sample such that the infrared rays reflect off of the plane reflex mirror on both sides of the area of intersection.

18. The method of claim 9, wherein said step of projecting comprises projecting the infrared rays at the solid state sample at an angle that is closer to parallel to the plane reflex mirror than to perpendicular to the plane reflex mirror, wherein said step of positioning comprises positioning the solid state sample so as to extend through a slit in the plane reflex mirror, and said step of projecting further comprises projecting the infrared rays at one of the front surface and the reverse surface of the solid state sample such that the infrared rays reflect off of the plane reflex mirror on both sides of and centered on the slit.

19. The method of claim 18, wherein said step of placing comprises placing a light transmissible solid state sample having a semiconductor surface as one of the front and reverse surfaces.

20. An apparatus, comprising:

an infrared light source for projecting infrared rays;

a plane reflex mirror for receiving infrared rays projected by said infrared light source;

a reflection spectrometer for receiving and evaluating infrared rays reflected by said plane reflex mirror; and support means for supporting a light transmissible solid state sample to be evaluated in an interaction region formed by reflected infrared rays such that infrared rays projected by said infrared light source are projected on a rear surface of the sample and such that the sample faces said plane reflex mirror.

21. The apparatus of claim 20, wherein said infrared light source comprises an interferometer and a polarizer is located between said interferometer and said plane reflex mirror for polarizing the infrared rays.

22. The apparatus of claim 21, and further comprising a reflex mirror for reflecting infrared rays from the interferometer to said polarizer and a reflex mirror for reflecting reflected infrared rays from said plane reflex mirror to said reflection spectrometer.

23. The apparatus of claim 20, wherein said reflection spectrometer comprises a detector for detecting reflected infrared rays and an instrumentation computer connected to said detector.

24. The apparatus of claim 20, and further comprising a light transmissible solid state sample to be evaluated that is supported by said support means above said plane reflex mirror, said sample having a semiconductor surface facing said plane reflex mirror.

25. An apparatus, comprising:

an infrared light source for projecting infrared rays;

a plane reflex mirror for receiving infrared rays projected by said infrared light source;

a reflection spectrometer for receiving and evaluating infrared rays reflected by said plane reflex mirror;

a slit in said plane reflex mirror for receiving a light transmissible solid state sample to be evaluated therein; and support means for supporting the light transmissible solid state sample to be evaluated in an upright position in said slit relative to said plane reflex mirror such that infrared rays projected by said infrared light source can be projected on a front or rear surface of the sample.

26. The apparatus of claim 25, wherein said infrared light source comprises an interferometer and a polarizer is located between said interferometer and said plane reflex mirror for polarizing the infrared rays.

27. The apparatus of claim 26, and further comprising a reflex mirror for reflecting infrared rays from the interferometer to said polarizer and a reflex mirror for reflecting reflected infrared rays from said plane reflex mirror to said reflection spectrometer.

28. The apparatus of claim 25, wherein said reflection spectrometer comprises a detector for detecting reflected infrared rays and an instrumentation computer connected to said detector.

29. The apparatus of claim 25, and further comprising a light transmissible solid state sample to be evaluated that is supported by said support means in said slit of said plane reflex mirror, said sample having a semiconductor surface.

30. An apparatus, comprising:

an infrared light source for projecting infrared rays;

a plane reflex mirror for receiving infrared rays projected by said infrared light source;

a reflection spectrometer for receiving and evaluating infrared rays reflected by said plane reflex mirror; and support means for supporting a light transmissible solid state sample to be evaluated in an upright position on said plane reflex mirror such that infrared rays projected by said infrared light source can be projected on a front or rear surface of the sample.

31. The apparatus of claim 30, and further comprising a light transmissible solid state sample to be evaluated that is supported by said support means on said plane reflex mirror, said sample having a semiconductor surface.

\* \* \* \* \*

UNITED STATES PATENT AND TRADEMARK OFFICE
CERTIFICATE OF CORRECTION

PATENT NO.   : 5,534,698
DATED        : July 9, 1996
INVENTOR(S)  : Hisayoshi Ohshima, et. al.

It is certified that error appears in the above-identified patent and that said Letters Patent is hereby corrected as shown below:

Title page, item [73] Assignee:  second  Assignee should be--Nippondenso Co., LTD.--.

Signed and Sealed this

Twenty-ninth Day of July, 1997

Attest:

BRUCE LEHMAN

*Attesting Officer*     *Commissioner of Patents and Trademarks*